US010111832B2

(12) United States Patent
Decorte et al.

(10) Patent No.: US 10,111,832 B2
(45) Date of Patent: Oct. 30, 2018

(54) ORODISPERSIBLE TABLETS OBTAINED BY COMPRESSION MOLDING

(71) Applicant: ETHYPHARM, St. Cloud (FR)

(72) Inventors: Isabelle Decorte, Beauvilliers (FR); Edouard Gendrot, Garnay (FR); Yann Prevost, Tremblay les Villages (FR)

(73) Assignee: ETHYPHARM, Saint-Cloud (FR)

( * ) Notice: Subject to any disclaimer, the term of this patent is extended or adjusted under 35 U.S.C. 154(b) by 76 days.

(21) Appl. No.: 14/652,328

(22) PCT Filed: Dec. 17, 2013

(86) PCT No.: PCT/FR2013/053113
§ 371 (c)(1),
(2) Date: Jun. 15, 2015

(87) PCT Pub. No.: WO2014/096669
PCT Pub. Date: Jun. 26, 2014

(65) Prior Publication Data
US 2015/0335581 A1    Nov. 26, 2015

(30) Foreign Application Priority Data

Dec. 17, 2012  (FR) ..................................... 12 62175

(51) Int. Cl.
| *A61K 9/20*  | (2006.01) |
| *A61K 45/06* | (2006.01) |
| *A61K 9/00*  | (2006.01) |
| *A61K 9/16*  | (2006.01) |

(52) U.S. Cl.
CPC .......... *A61K 9/0056* (2013.01); *A61K 9/1623* (2013.01); *A61K 9/205* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 9/2081* (2013.01); *A61K 9/2095* (2013.01); *A61K 45/06* (2013.01)

(58) Field of Classification Search
CPC .. A61K 9/0056; A61K 9/1623; A61K 9/2077; A61K 9/2081; A61K 9/2095; A61K 45/06; A61K 9/2027; A61K 9/2013; A61K 9/205; A61K 9/2009; A61K 9/2054; A61K 9/2018
See application file for complete search history.

(56) References Cited

U.S. PATENT DOCUMENTS

| 5,501,861 | A  |   | 3/1996  | Makino   |             |
|-----------|----|---|---------|----------|-------------|
| 6,287,596 | B1 | * | 9/2001  | Murakami | A61K 9/0056 |
|           |    |   |         |          | 424/435     |
| 6,743,443 | B1 |   | 6/2004  | Furitsu   |             |
| 7,829,122 | B2 |   | 11/2010 | Bruna    |             |
| 2003/0215496 | A1 | * | 11/2003 | Patel | A61K 9/1617 |
|           |    |   |         |          | 424/452     |
| 2005/0013857 | A1 | * | 1/2005 | Fu | A61K 9/0056 |
|           |    |   |         |          | 424/464     |
| 2005/0019391 | A1 | * | 1/2005 | Gendrot | A61K 9/2081 |
|           |    |   |         |          | 424/464     |
| 2009/0087485 | A1 | * | 4/2009 | Pilgaonkar | A61K 9/0056 |
|           |    |   |         |          | 424/464     |
| 2009/0123543 | A1 | * | 5/2009 | Pilgaonkar | A61K 9/1682 |
|           |    |   |         |          | 424/480     |
| 2009/0148524 | A1 | * | 6/2009 | Higuchi | A61K 9/0056 |
|           |    |   |         |          | 424/470     |
| 2012/0295916 | A1 |   | 11/2012 | Winter |             |

FOREIGN PATENT DOCUMENTS

| AU | 752270       |    | 9/2002  |              |
|----|--------------|----|---------|--------------|
| AU | 758299       |    | 3/2003  |              |
| CA | 2092074      |    | 1/1993  |              |
| EP | 1523974      |    | 4/2005  |              |
| EP | 1681048      |    | 7/2006  |              |
| EP | 2138165 A1   | *  | 12/2009 | ........... A61K 9/2009 |
| FR | 2679451      |    | 1/1993  |              |
| FR | 2761605      |    | 10/1998 |              |
| FR | 2778848      |    | 11/1999 |              |
| FR | 2816507      |    | 5/2002  |              |
| JP | 2011006482 A | *  | 1/2011  | ........... A61K 9/0056 |
| WO | 03039520     |    | 5/2003  |              |
| WO | 2005105049   |    | 11/2005 |              |
| WO | 2007113856   |    | 10/2007 |              |
| WO | 2009123626   |    | 10/2009 |              |

OTHER PUBLICATIONS

English translation of JP-2011006482-A. Translated on Jul. 19, 2018 from J-Plat Pat (Japan Platform for Patent Information).*
International Search Report dated Mar. 4, 2014 for International Application No. PCT/FR2013/053113.
Written Opinion of the International Searching Authority dated Mar. 4, 2014 for International Application No. PCT/FR2013/053113.

* cited by examiner

*Primary Examiner* — Doan T Phan
(74) *Attorney, Agent, or Firm* — Dinsmore & Shohl LLP

(57) ABSTRACT

Embodiments of the present invention provide an orodispersible tablet having a hardness of 30 to 80 N, and preferably 40 to 75 N, a brittleness less than 1% and preferably less than 0.5%, disintegrating in the mouth within 60 seconds and preferably within 40 seconds, comprising an active ingredient in the form of coated microcrystals or microgranules and a mixture of excipients chosen from a group comprising a diluent, a disintegrant, a sweetener, a binder, a levelling agent, a humectant or wetting agent, a lubricant, a flavoring agent, a dye, and mixtures thereof, said mixture of excipients preferably coming in the form of grains.

3 Claims, 3 Drawing Sheets

ORODISPERSIBLE TABLETS OBTAINED BY COMPRESSION MOLDING

CROSS-REFERENCE TO RELATED APPLICATIONS

This application is a U.S. National Phase Application of International Application No. PCT/FR2013/053113, filed Dec. 17, 2013, which claims the benefit of priority of French Application No. 12 62175, filed Dec. 17, 2012, the contents of which applications are incorporated by reference herein, in their entireties and for all purposes.

FIELD OF THE INVENTION

The present invention relates to the field of pharmacy, and more particularly to that of galenic.

The subject of the invention is an orodispersible tablet obtained by compression molding.

BACKGROUND OF THE INVENTION

An orodispersible tablet is a solid form that disintegrates or dissolves in the mouth, solely on contact with saliva, generally in less than 60 seconds.

Orodispersible tablets are a galenical form that is on the rise, which has greatly developed in recent years. The reason for this is that orodispersible tablets have many advantages and are particularly suited to patients who have difficulties in swallowing, for example children and the elderly. However, these populations are not the only ones presenting with dysphagia, since about 30 to 50% of the population is concerned by this problem. Many adults are also concerned, and especially patients with psychiatric disorders, but also those suffering from thyroid complaints, Parkinson's disease, immune system deficiency diseases (AIDS), gastrointestinal reflux, and also patients suffering from nausea, vomiting or travel sickness. Orodispersible tablets are also suitable for people who do not have ready access to water, especially when travelling. Another advantage of said tablets is that they allow a practical and discreet use.

To allow rapid disintegration, orodispersible tablets have a porous structure and are compressed at lower pressures than conventional tablets, the drawbacks being that they may be more fragile and difficult to handle.

A large number of methods for obtaining orodispersible tablets have been developed in recent years.

However, there are still at the present time certain characteristics that limit the industrial development of orodispersible tablets, especially their excessive friability and their occasionally unpleasant taste and mouthfeel.

Thus, although orodispersible tablets remain a fairly widespread form that patients appreciate, especially for their practical and rapid use, a study performed by the Applicant has shown that the taste and mouthfeel of a tablet appear to be the most important parameters for patients, and thus the unpleasant taste and/or unpleasant mouthfeel are one of the major causes of non-compliance with medical treatments, and thus of their failure.

One of the aims of the invention is thus to obtain an orodispersible tablet that has a pleasant mouthfeel and/or a pleasant taste in the mouth.

More precisely, one of the aims of the invention is to obtain an orodispersible tablet that has a disintegration time in the mouth of less than 60 seconds, preferably less than 40 seconds and even more preferentially less than 30 seconds, which has satisfactory friability, while at the same time having a pleasant taste and mouthfeel.

In patent application WO 03/039520, the described orodispersible tablets are obtained via a "direct compression" method, the main steps of which are summarized in FIG. 1. However, this direct compression method is not always entirely satisfactory, especially in terms of the friability and the disintegration time of the tablets thus obtained.

The Applicant has now found, surprisingly, that orodispersible tablets with very satisfactory properties, as described above, could be obtained when they were prepared via a process known to those skilled in the art as compression molding.

Molding is a method in which the tablets are formed by compression of a wet powder, by solidification of a gel or by evaporation of a solvent. In the three cases, drying of the tablets or evaporation of the solvent takes place after forming the tablets. Three different molding methods exist: compression molding, heat molding and no-vacuum lyophilization.

Conventionally, the compression molding method is based on the compression of a wet mixture. This method comprises several steps: a powder mixture is moistened with an aqueous-alcohol solvent, and this wet mixture is then compressed at compression forces lower than those used in direct compression, which leads to a very porous structure. The large porosity of the tablets thus obtained allows very rapid disintegration (from 5 to 15 seconds). The tablets are then dried to remove the solvent therefrom.

The compression molding process usually uses soluble excipients (saccharides) which also contributes towards rapid disintegration and gives a pleasant taste and mouthfeel. The hardness may be very variable from one formulation to another. This is a difficult parameter to adjust, but it would appear that it is possible to obtain hardnesses higher than those obtained in direct compression.

In U.S. Pat. No. 5,501,861, a compression molding method was developed, in which a wet mixture of active principle, starches and sugars is compressed so as to obtain porous tablets, having a hardness sufficient for manufacture and a disintegration time of less than a minute. A similar method was also developed in U.S. Pat. No. 6,743,443.

SUMMARY OF THE INVENTION

The studies performed by the Applicant have now made it possible to discover that when orodispersible tablets (1) were prepared via a compression molding process and (2) when they had a certain formulation of wet excipients, preferably wet granulated, then said tablets had particularly advantageous properties, in terms of hardness, friability and also mouthfeel (and, of course, in terms of the disintegration time).

DETAILED DESCRIPTION OF THE INVENTION

Figure 1:
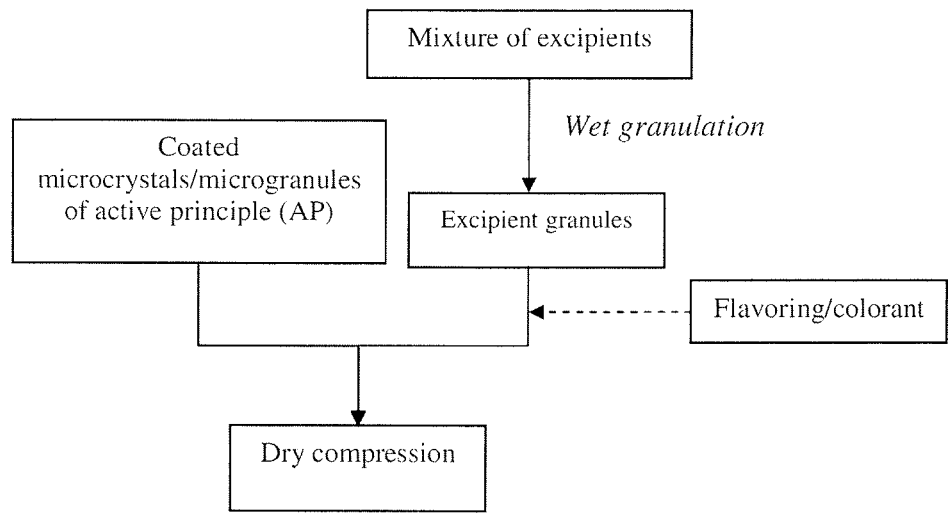
FIG. 1 represents the main steps in the direct compression method used in patent application WO 03/039520 filed in the name of the Applicant.
Figure 2:
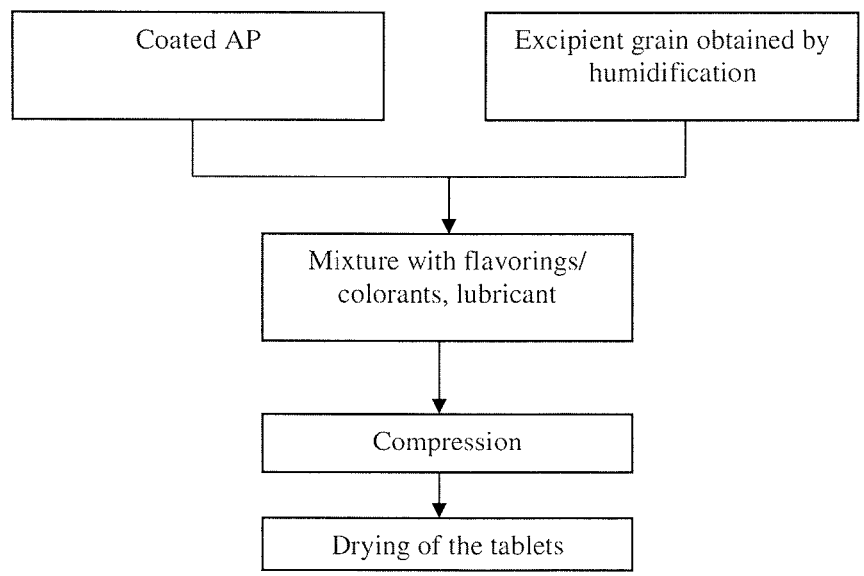
FIG. 2 represent the compression molding method according to the invention.

According to a first subject, the present invention relates to an orodispersible tablet with a hardness ranging from 30 to 80 N and preferably from 40 to 75 N, a friability of less than 1% and preferably less than 0.5%, a disintegration in the mouth of less than 60 seconds and preferably less than 40 seconds, comprising an active principle in the form of coated microcrystals or microgranules and a mixture of excipients chosen from the group comprising a diluent, a disintegrant, a sweetener, a binder, a flow agent, a humectant or wetting agent, a lubricant, a flavoring agent, a colorant and mixtures thereof, said mixture of excipients preferably being in the form of grains, characterized in that said tablet is obtained via a compression molding process comprising the following steps:
  preparing by wetting the mixture of excipients, preferably in the form of grains, having a residual humidity or water content ranging from 0.5% to 7%, preferably from 1% to 5%, and more preferentially from 2% to 4%,
  preparation of coated microcrystals or microgranules of active principle,
  mixing of the coated microcrystals or microgranules of active principle and of the wet mixture of excipients as prepared above, said mixture of excipients preferably being in the form of grains,
  optionally, adding to the wet mixture for compression, as prepared above, of excipients chosen from the group comprising a flow agent, a lubricant, a flavoring, a sweetener, a colorant and mixtures thereof,
  compression of the mixture for compression prepared above to obtain a tablet,
  optionally, drying of the tablet thus obtained.

The wet mixture of excipients may be either in the form of a wet powder or in the form of wet grains.

The terms "wet mixture of excipients" or "mixture of wet excipients" have the same meaning and may be used without preference in the text hereinbelow.

When the wet mixture of excipients is in the form of wet grains, the compression properties of the mixture during the preparation of the tablet are improved. Thus, according to the invention, the wet mixture of excipients is preferably in the form of wet grains of excipients.

The term "wetting" means a step of moistening of the mixture of excipients. This first step of the process is distinguished from wet granulation, which comprises the use of a much larger amount of solvent so as to wet the mixture and to increase the particle size of the mixture. During wet granulation, a step of drying of the grains is also necessary before compressing the mixture.

For the purposes of the present invention, an orodispersible tablet is a tablet which disintegrates or dissolves in the mouth, solely on contact with saliva, without supplying water and without being chewed, in less than 60 seconds, preferably less than 40 seconds and even more preferentially less than 30 seconds, forming a suspension that is easy to swallow.

The disintegration time in the mouth corresponds to the time that separates, on the one hand, the moment at which the tablet is placed in the mouth on contact with saliva and, on the other hand, the moment at which the suspension resulting from the disintegration of the tablet on contact with saliva is swallowed. This disintegration time corresponds to the in vivo disintegration time.

It is also possible to measure the in vitro disintegration time of the orodispersible tablets according to the invention. This disintegration time is measured according to European Pharmacopea 2.9.1 on an Erweka ZT 31 machine or any other machine for measuring the disintegration time of tablets, corresponding to European Pharmacopea 2.9.1. The in vitro disintegration time of the tablets according to the invention is from 10 to 20 seconds.

The tablets obtained by compression molding are as hard as those obtained by direct compression, but they have the advantage of disintegrating more rapidly than those obtained by direct compression.

According to an advantageous embodiment of the invention, the mixture of excipients comprises at least one humectant.

According to the invention, the terms "humectant" and "humectant agent" have the same meaning as "wetting agent" and may therefore be used without preference in the text hereinbelow.

According to an advantageous embodiment of the invention, the humectant is chosen from the group comprising poloxamers, preferably "poloxamer 188" or "poloxamer 407", macrogols, macrogol glycerides, polysorbates, said humectant preferably being a macrogol glyceride such as stearoyl macrogol-32 glyceride or lauroyl macrogol-32 glyceride sold under the name Gelucire® 44/14.

According to an advantageous embodiment of the invention, the mixture of excipients, preferably in the form of grains, comprises:
  from 65% to 90% and preferably from 70% to 80%, of a diluent chosen from the group comprising mannitol, xylitol, sorbitol, maltitol and mixtures thereof, said diluent preferably being mannitol sold under the name Mannitol 60,
  from 2% to 25% and preferably from 10% to 20%, of a disintegrant chosen from the group comprising crospovidone, sodium croscarmellose (AcDiSol®), sodium carboxymethyl starch (Explotab®) and mixtures thereof, said disintegrant preferably being crospovidone sold under the name Polyplasdone® XL,
  from 1% to 8% and preferably from 3% to 5% of a sweetener chosen from the group comprising aspartame, potassium acesulfame, sodium saccharinate, sucralose and mixtures thereof, said sweetener preferably being aspartame,
  from 3% to 10% and preferably from 5% to 8%, of a binder chosen from the group comprising weakly substituted hydroxypropylcellulose, gum arabic, corn starch, pregelatinized starch, maltodextrins and mixtures thereof, said binder preferably being gum arabic and/or hydroxypropylcellulose sold under the name L-HPC LH 21,
  from 0% to 5% and preferably from 1% to 3% of a flow agent chosen from the group comprising silica, preferably that sold under the name Syloid® 244 FP, hydrophobic colloidal silica, preferably that sold under the name Aerosil R® 972, precipitated silica, preferably that sold under the name Aerosil® 200, and mixtures thereof,
  from 0 to 5% and preferably from 0.1% to 3% of a humectant, said humectant being as defined previously,
  from 0 to 5% of a lubricant, said lubricant preferably being a hydrophilic lubricant chosen from the group comprising sodium stearyl fumarate, sodium lauryl sulfate, said hydrophilic lubricant preferably being sodium stearyl fumarate sold, for example, under the name Pruv®, from 0 to 8% and preferably from 0.5% to 4% of a flavoring agent and/or colorant, water qs 100%, the percentages being weight percentages relative to the total weight of the mixture of excipients, said mixture of excipients preferably being in the form of grains.

The flavoring agent and the colorant that may be included in the constitution of the mixture of excipients, preferably in the form of grains, are chosen from those that are pharmaceutically acceptable. They are chosen according to the organoleptic characteristics desired for the orodispersible tablet and so as best to mask the residual taste of the active principle.

According to a particular embodiment of the invention, the preparation of the wet mixture of excipients, preferably in the form of grains, is performed by wetting the mixture of excipients, preferably in the form of grains, using a wetting solution chosen from the group comprising water, an aqueous wetting solution, a humectant or wetting agent, an alcoholic solution and mixtures thereof, said wetting solution being incorporated into the mixture of excipients, preferably in the form of grains, in an amount making it possible to obtain a wet mixture of excipients, preferably in the form of grains, having a residual humidity ranging from 0.5% to 7%, preferably from 1% to 5% and more preferentially from 2% to 4%.

Thus, according to the invention, a wet mixture of excipients denotes a mixture of excipients with a residual humidity ranging from 0.5% to 7%, preferably from 1% to 5% and more preferably from 2% to 4%.

In the text hereinabove and hereinbelow, when the mixture of excipients is in the form of grains, then the wet mixture of excipients obviously denotes wet grains of excipients.

The residual humidity is measured either via the Karl Fisher method or with a desiccation balance (15 minutes at 80° C.).

Advantageously, the wetting solution comprises an aqueous wetting solution and a humectant, said humectant being preferably lauroyl macrogol-32 glyceride sold under the name Gelucire® 44/14.

According to another advantageous embodiment, the wetting solution comprises water and a humectant as defined above.

According to yet another advantageous embodiment, water is used as wetting solution for the wet granulation.

According to a particular embodiment of the invention, certain excipients of the orodispersible tablet are not present in the wet mixture of excipients, preferably in the form of grains, but are added in addition to the wet mixture of excipients, preferably in the form of grains, into the mixture for compression. These excipients are chosen from the group comprising:

from 1% to 5%, preferably from 2% to 4%, of a flow agent, from 1% to 5%, preferably from 2% to 4%, of a lubricant, from 0 to 5% and preferably from 0.5% to 4% of a flavoring agent and/or a colorant, said flow agents and lubricant being as defined previously, the percentages being weight percentages relative to the total weight of the mixture for compression.

Thus, certain excipients such as the flow agent, the lubricant, the flavoring agent and/or the colorant may be introduced:

during the preparation of the wet mixture of excipients, for example during the manufacture of the wet grain (granulated) of excipient and/or after manufacture of the wet grain of excipient, by mixing during the preparation of the mixture for compression.

According to an advantageous embodiment of the invention, the mixture for compression comprises:

from 5% to 40%, preferably from 10% to 30% and even more preferentially from 15% to 25% of coated microcrystals or microgranules of active principle, from 55% to 95%, preferably from 65% to 85% and even more preferentially from 70% to 80% of the wet mixture of excipients, preferably in the form of grains, from 0 to 10%, preferably from 1% to 7% and even more preferentially from 2% to 5% of excipients that are not present in the wet mixture of excipients, preferably in the form of grains, the percentages being weight percentages relative to the total weight of the mixture for compression.

According to the invention, the mixture for compression has a residual humidity or water content ranging from 0.1% to 6% and preferably from 2% to 3%.

According to another advantageous embodiment of the invention, the mixture for compression is compressed using compression forces ranging from 8 to 22 kN (kNewtons), preferably from 10 to 20 kN and even more preferentially from 12 kN to 18 kN.

According to another advantageous embodiment, the drying of the tablet obtained after the compression step is performed at a temperature ranging from 35 to 65° C., preferably from 45 to 55° C., for a time ranging from 30 minutes to 3 hours and preferably from 1 to 2 hours.

As a guide, the orodispersible tablet of the invention before drying has a hardness ranging from 45 to 80 N and preferably from 50 to 75 N, whereas after drying it has a hardness ranging from 30 to 70 N and preferably from 30 to 65 N.

The method for measuring the hardness comes from the European Pharmacopea 2.9.8.

As a guide, the orodispersible tablet of the invention before drying has a friability of less than 0.8% and preferably ranging from 0.2 to 0.7%, whereas after drying it has a friability of less than 0.4% and preferably ranging from 0.1 to 0.3%.

The friability is measured on an Erweka TA 10 machine according to the method described in the European Pharmacopea (edition 7, chapter 2.9.7.) On account of this satisfactory friability, it is possible to use conventional industrial methods for transferring and packaging the tablets that do not require special precautions and allow great speed of execution.

Another subject of the present invention is a process for preparing an orodispersible tablet, comprising the steps of:

preparation by wetting of a mixture of excipients, said mixture of excipients preferably being in the form of grains, said mixture of excipients being chosen from the group comprising a diluent, a disintegrant, a sweetener, a binder, a flow agent, a humectant or wetting agent, a lubricant, a flavoring agent, a colorant and mixtures thereof, said mixture of excipients having a residual humidity or water content ranging from 0.5% to 7%, preferably from 1% to 5% and more preferentially from 2% to 4%, preparation of coated microcrystals or microgranules of active principle, mixing of the coated microcrystals or microgranules of active principle, on the one hand, and of the wet mixture of excipients, on the other hand, said wet mixture of excipients preferably being in the form of wet grains of excipients, optionally, adding to the wet mixture for compression, as prepared above, of excipients chosen from the group comprising a flow agent, a lubricant, a flavoring, a sweetener and mixtures thereof, compression of the mixture for compression prepared above to obtain a tablet, optionally, drying of the tablet thus obtained.

Said excipients used in the preparation process of the invention, and in particular said diluent, disintegrant, sweetener, binder, flow agent, humectant, lubricant, flavoring agent and colorant are as defined previously as regards their nature and/or amount.

According to an advantageous embodiment of the process of the invention, the mixture of excipients comprises at least one humectant chosen from the group comprising poloxamers, preferably "poloxamer 188" or "poloxamer 407", macrogols, macrogol glycerides, polysorbates, said humectant preferably being a macrogol glyceride such as stearoyl macrogol-32 glyceride or lauroyl macrogol-32 glyceride sold under the name Gelucire® 44/14.

According to another advantageous embodiment of the process of the invention, the preparation of the wet mixture of excipients, preferably in the form of grains, is performed by wetting the mixture of excipients using a wetting solution chosen from the group comprising water, an aqueous wetting solution, a humectant, an alcoholic solution and mixtures thereof, said wetting solution being incorporated into the mixture of excipients in an amount making it possible to obtain a mixture of excipients having a residual humidity as defined above, said wet mixture of excipients preferably being in the form of wet grains.

The invention also relates to an orodispersible tablet that may be obtained according to the process as described above, characterized in that it has:

a hardness ranging from 30 N to 80 N, preferably from 40 to 75 N and/or, a friability of less than 1% and preferably less than 0.5%.

According to a particular embodiment of the invention, the orodispersible tablet as defined above also has:

little or no core effect in the mouth, and/or a pleasant mouth texture and/or a pleasant taste in the mouth.

For the purposes of the present invention, the term "core effect" characterizes a more substantial agglomeration of particles at the center of the tablet, which remains hard for longer and persists in the mouth, whereas the outer layers of the tablet disintegrate more rapidly.

Thus, if a core effect exists, the disintegration time in the mouth is prolonged. Preferably, the core effect should be as low as possible.

For the purposes of the invention, a pleasant mouth feel denotes a pleasant texture in the mouth, i.e. the absence of a pasty or granular sensation and/or a pleasant taste in the mouth.

By way of example, the orodispersible tablet of the invention has:

a mass ranging from 200 to 600 mg and preferably from 300 to 500 mg, a thickness ranging from 1 to 5 mm and preferably from 2 to 4 mm, a diameter from 8 to 14 mm and preferably from 9 to 12 mm.

Thus, such tablets are much too large to be swallowed, but may readily be placed in the oral cavity, on the tongue, where they disintegrate due to the presence of saliva and of the natural pressure exerted between the tongue and the palate when the mouth is closed.

According to another embodiment, the tablets may comprise at least one notch allowing them to be split so as to administer a smaller amount of active principle.

The orodispersible tablet of the invention is suitable for the use of any type of active principle that is in the form of microcrystals or that may be granulated.

By way of example, the active principle may be chosen from the group comprising the gastrointestinal sedatives, antacids, antalgic agents, anti-inflammatories, coronary vasodilators, peripheral and cerebral vasodilators, anti-infectious agents, antibiotics, antivirals, antiparasitics, anticancer agents, anxiolytic agents, neuroleptic agents, central nervous system stimulants, antidepressants, antihistamines, antidiarrhetics, laxatives, food supplements, immunodepressants, hypocholesterolemiants, hormones, enzymes, antispasmodic agents, antiangina agents, medicaments influencing the cardiac rhythm, medicaments used in the treatment of arterial hypertension, antimigraine agents, medicaments influencing the blood coagulability, antiepileptics, muscle relaxants, medicaments used in the treatment of diabetes, medicaments used in the treatment of thyroid dysfunctions, diuretics, anorexigenic agents, antiasthmatic agents, expectorants, antitussive agents, mucoregulators, decongestants, hypnotic agents, antinausea agents, hematopoietic agents, uricosuric agents, plant extracts and contrast agents.

The orodispersible tablet of the invention is particularly suited to the active principles that are useful in treatments intended for children or the elderly, taking into account their ease of taking.

The active principle is present in the orodispersible tablet in the form of coated microcrystals or microgranules.

The active principle particles have a size ranging from 10 to 500 μm.

The coating of the microcrystals or microgranules of active principle may be performed according to one of the methods described in patent applications FR 91/09245, FR 97/04234, FR 98/06384 and FR 0 014 803.

The composition of the functional coating layer is chosen as a function of the desired characteristics in terms of taste masking and/or release of active principle.

According to a preferred embodiment of the invention, when the mixture of excipients is in the form of grains, said grains have a median particle size of between +30% and −30%, preferably between +10% and −10%, relative to the dimension of the coated microcrystals or microgranules.

According to an advantageous embodiment, the orodispersible tablet of the invention is such that the mean size of the coated microcrystals or microgranules of active principle is from 100 μm to 500 μm, preferably from 200 μm to 400 μm, and the size of the excipient grains is from 70 μm to 650 μm, preferably from 180 μm to 440 μm.

The invention will be understood more clearly in the light of the nonlimiting and purely illustrative examples that follow and of the figures.

In the text hereinbelow, the following abbreviations will be used:

AP: Active Principle
ODT: "Orally Disintegrating Tablet", i.e. an orodispersible tablet
FT or ODT FT: reference Flashatb® orodispersible tablet (obtained by direct compression)
DC or ODT DC: orodispersible tablet obtained by direct compression
Hum or ODT Hum: orodispersible tablet obtained according to the process of the invention
RH: Residual Humidity, water content
KF: Karl Fischer
LOD: "Loss On Drying"
m/m: mass/mass
Ave: average
ND: not done FIGS. 1 to 5 make it possible, on the one hand, to illustrate a method of the prior art for preparing orodispersible tablets, and, on the other hand, to illustrate the examples below.

EXAMPLES

All the ODTs tested below are placebos. However, to mimic the active principle, 20% of "Neutrals", namely a "mimic" of the coated granules of active principle, having a diameter ranging from 500 to 600 μm, were incorporated into the ODTs.

Specifically, all the active principles used by the Applicant in the ODTs are coated so as to mask their taste, which explains the relatively large particle size. The particular grade of Neutrals was chosen for reasons of industrial availability.

Orodispersible tablets as obtained in patent application WO 03/039520, by direct compression, are represented without preference in the text hereinbelow by "Flashtab®", FT or ODT FT, and are prepared so as to be able to compare them with the ODTs of the invention (represented in the text hereinbelow by Hum or ODT Hum).

Example 1 (Comparative): Preparation of the "ODT FT" by Direct Compression

Materials and Methods

The starting materials used in the ODT FTs are indicated in table 1.

TABLE 1

| Names | Manufacturer | Function |
|---|---|---|
| Neutrals 500/600 | NP Pharm | AP mimic |
| Pearlitol ® SD 200 and 160C | Roquette | Diluent |
| Polyplasdone ® XL | ISP | Disintegrant |
| Aspartame | Ajimoto | Sweetener |
| Syloid ® 244 FP | Grace Davison | Flow agent |
| Magnesium stearate | Peter Greven | Lubricant |

The preparation of the mixtures is performed in a Lodige type FM 50 E machine (ploughshare granulator) and then in Frogerais 27 or 60 L cubic mixers.

Drying is performed in a Binder APT.line™ FP oven equipped with perforated trays.

The mixture is compressed on a Fette P1200 rotary press equipped with mechanical feed assistance.

The mass, thickness and hardness of the tablets are controlled on a Checkmaster 4 Fette machine.

The friability is measured on an Erweka TA 10 machine according to the method described in the European Pharmacopea (edition 7, chapter 2.9.7.).

The in vitro disintegration tests are performed on six ODT FT tablets on an Erweka ZT 31 machine.

Measurement of the residual humidity is performed on a Karl Fischer Mettler Toledo DL 31 machine and also on a Moisture Analyzer Mettler Toledo HR 83 and Sartorius MA 100 machine.

The density measurements are performed on a Vankel Tap density machine according to the method described in the European Pharmacopea (edition 7.0, chapter 2.9.34.). The Carr index is also calculated according to the European Pharmacopea.

Table 2 below represents the composition of the mixture for compression of the ODT FTs.

TABLE 2

| ODT FT | |
|---|---|
| Names | Percentages |
| Neutrals 500/600 | 20.0 |
| Pearlitol ® SD 200 | 42.0 |
| Pearlitol ® 160C | 26.5 |
| Polyplasdone ® XL | 7.0 |
| Aspartame | 2.0 |
| Syloid ® 244 FP | 1.0 |
| Magnesium stearate | 1.5 |
| TOTAL | 100.0 |

The reference ODT FTs are manufactured by direct compression. The mixture is compressed on a Fette P1200 rotary press, with punches of 12 mm of diameter of round, flat, beveled type. The target hardness values are 50 and 70 N.

The mass, the thickness, the hardness, the friability and the disintegration time of the tablets obtained are measured. The mass, thickness and hardness measurements are performed on 10 tablets 12 mm in diameter.

In vivo tests were performed on the ODT FTs. These tests were performed by 11 adult volunteers. Each volunteer tested on average 4 to 6 tablets, with the possibility of drinking between each intake, if necessary. Each tablet was tested by three people.

The parameters evaluated are:
the in vivo time of disintegration in the mouth (chronometered),
the presence or absence of a core effect,
the mouthfeel.

Results and Discussion

Table 3 below indicates the characteristics of the ODT FTs (the composition of which is indicated in table 2), as a function of the compression forces exerted.

TABLE 3

| | | | ODT FT | | | | | |
|---|---|---|---|---|---|---|---|---|
| Hardness | Compression | Drying | Mass | Thickness | Friability | in vitro disint. (s) | | Flow of the |
| (N) | force (kN) | (h) | (mg) | (mm) | (%) | min | max | mixture |
| 46 | 11.0 | 0 | 447 | 3.46 | 0.41 | 12.7 | 17.7 | Good |
| 73 | 15.7 | 0 | 445 | 3.33 | 0.15 | 16.2 | 21.9 | |

Table 4 below represents the in vivo tests for said ODT FTs (obtained by direct compression).

TABLE 4

| Disint. in mouth (s) | Core effect | Mouthfeel |
|---|---|---|
| 33 | large | Disintegration slow to start |

In the mouth, the tablets have a large core effect, a quite pleasant mouthfeel, but disintegration that is slow to start, although the disintegration time is satisfactory.

Example 2

The starting materials used are indicated in table 5 below.

TABLE 5

| Names | Manufacturer | Function |
|---|---|---|
| Neutrals 500/600 | NP Pharm | AP mimic |
| Mannitol 60 | Roquette | Diluent |
| Polyplasdone ® XL | ISP | Disintegrant |
| Aspartame | Ajimoto | Sweetener |
| Syloid ® 244 FP | Grace Davison | Flow agent |
| Aerosil ® R 972 | Evonik | Flow agent |
| L-HPC LH 21 | Seppic | Binder and disintegrant |
| Pruv ® | JRS Pharma | Hydrophilic lubricant |
| Aerosil ® 200 | Evonik | Flow agent |
| Gum arabic | Carlo Erba | Binder |
| Gelucire ® 44/14 | Gattefossé | Humectant |
| AcDiSol ® | FMC Biopolymer | Disintegrant |
| Explotab ® | JRS Pharma | Disintegrant |

The machines used are the same as those described in example 1 above.

The mixture in the form of grains is prepared in a Lodige machine and the excipients for compression are then added as an external phase (Syloid®, Aerosil®, Pruv®) with the Neutrals 500/600. This mixture is compressed using 12 mm punches (round, flat, beveled type).

The target hardness values of 50 and 70 N are targeted for each test.

For each type of tablet obtained, the mass, thickness, hardness, friability and disintegration time are measured. The mass, thickness and hardness measurements are performed on 10 tablets.

For the direct compression test, the friability and disintegration tests were performed only once on account of the small sizes of the batches.

For all the following tests with wetting, the tests were performed three times using the same batch. The tablets are stored in glass bottles so as to protect them from moisture.

For the in vivo tests, the method is the same as that described in example 1.

Using these starting materials, tablets were prepared by direct compression ODT DC (for comparative purposes) and tablets according to the invention were prepared by compression molding.

Preparation of the ODT DCs (Comparative)

Table 6 below indicates the percentage composition of the mixture for compression making it possible to obtain an ODT DC, the relative humidity of this mixture is given in table 7.

TABLE 6

| ODT DCs | |
|---|---|
| Names | Percentages |
| Neutrals 500/600 | 20.00 |
| Mannitol 60 | 53.00 |
| Polyplasdone XL | 13.40 |
| Aspartame | 4.50 |
| L-HPC LH 21 | 4.70 |
| Syloid ® FP 244 | 0.90 |
| Aerosil ® R 972 | 2.00 |
| Pruv ® | 1.50 |
| Total | 100.00 |

TABLE 7

| | LOD (%) | KF (%) |
|---|---|---|
| Mixture for compression | 1.4 | 1.5 |

The compression is performed on the same type of machine as in example 1, at two different compression forces to target a hardness of 50 N or 70 N.

The same tests as in example 1 were performed.

Table 8 below indicates the characteristics of the ODT DCs (obtained by direct compression).

TABLE 8

| Hardness | Compression | Drying | Mass | Thickness | Friability | in vitro disint. (s) | |
|---|---|---|---|---|---|---|---|
| (N) | force (kN) | (h) | (mg) | (mm) | (%) | min | max |
| 46 | 20.0 | 0 | 457 | 3.41 | 0.50 | 21 | 24 |

The results of the in vivo tests are given in table 9.

TABLE 9

| ODT DC | | |
|---|---|---|
| Disint. in mouth (s) | Core effect | Mouthfeel |
| 30 | large | Long disintegration, slightly pasty |

Preparation of Tablets According to the Invention (Compression Molding Method)

A formula similar to that of the direct compression test is reproduced, but this time using the humidification method (Hum). The mixture for compression is prepared from a wet mixture of excipients in the form of wet grains mixed with the Neutrals 500/600.

One portion of the excipients forms the grains, the other portion of the excipients (namely those that do not form the excipient grains) is added as external phase.

In a first stage, excipient grains having the percentage composition given in table 10 are prepared.

A value of 3% residual humidity (RH) is targeted for the excipient grains. The amount of water is added gradually, with regular controlling of LOD, until the desired RH value (3%) is obtained.

TABLE 10

| Names | Percentages (dry extract) | Percentages |
|---|---|---|
| Mannitol 60 | 71.14 | 69.59 |
| Polyplasdone XL | 17.85 | 17.46 |
| Aspartame | 3.36 | 3.29 |
| L-HPC LH 21 | 6.31 | 6.17 |
| Syloid FP 244 | 1.34 | 1.31 |
| Water |  | 2.22 |
| Total | 100 | 100 |

The excipient grains are then mixed with the Neutrals 500/600 and the additional excipients, so as to obtain the mixture for compression, the percentage composition of which is given in table 11.

TABLE 11

| Names | Percentages |
|---|---|
| Neutrals 500/600 | 20.09 |
| Mixture of excipients in the form of grains | 76.00 |
| Syloid FP 244 | 1.95 |
| Pruv ® | 1.95 |
| Total | 100.00 |

Table 12 below represents the residual humidity measured for the mixture of wet excipients, in the form of wet grains, and for the mixture for compression, the compositions of which are, respectively, given in tables 11 and 12.

TABLE 12

|  | LOD (%) | KF (%) |
|---|---|---|
| Mixture of excipients in the form of grains | 3.0 | 2.9 |
| Mixture for compression | 2.6 | 2.7 |

For all the humidification tests, the degree of RH is measured on the tablets by means of the Karl Fischer method.

The residual humidity is about 3% for the tablets without drying (non-dried ODT Hum) and about 1.5% for the tablets dried for 2 hours (dried ODT Hum).

The mixture for compression is compressed using the same machine as in example 1 and at two different compression forces to achieve hardness values of 50 N or 70 N. The hardness of the tablets is measured on the tablets exiting the compressor or after drying for 1 h or 2 h at 50° C.

Table 13 below gives the characteristics of the ODT Hums of the invention, said characteristics depending on the compression force exerted (12.5 kN or 16.4 kN) and the drying time (0, 1 or 2 h).

TABLE 13

| Hardness (N) | Compression force (kN) | Drying (h) | Mass (mg) | Thickness (mm) | Friability (%) | in vitro disint. (s) min | in vitro disint. (s) max | Carr index |
|---|---|---|---|---|---|---|---|---|
| 48 | 12.5 | 0 | 450 | 3.26 | 0.69 | 13.6 | 15.8 | 21 |
| 43 |  | 1 | 444 | 3.27 | 0.43 | 13.6 | 16.5 |  |
| 41 |  | 2 | 444 | 3.26 | 0.48 | 14.4 | 16.2 |  |
| 73 | 16.4 | 0 | 450 | 3.16 | 0.22 | 13.7 | 17.6 |  |
| 59 |  | 1 | 443 | 3.16 | 0.13 | 15.8 | 20.1 |  |
| 56 |  | 2 | 439 | 3.42 | 0.07 | 16.0 | 17.8 |  |

Table 14 represents the in vivo tests for ODT Hum tablets at 50 N.

TABLE 14

| ODT Hum 50 N | | | | |
|---|---|---|---|---|
| Hardness (N) | Drying time (h) | Disint. in mouth (s) | Core effect | Mouthfeel |
| 50 | 0 | 26 | Little or none | Not granular, pleasant |
|  | 2 | 24 | low | Slightly more pasty |

The various tablets obtained by the direct compression method (ODT DC) and the humidification method (ODT Hum) are compared with each other and with Flashtab® tablets (ODT FT of example 1) as regards their friability, their disintegration time in the mouth, the core effect and the mouthfeel. The processes are also compared in terms of compression force.

Figure 3:
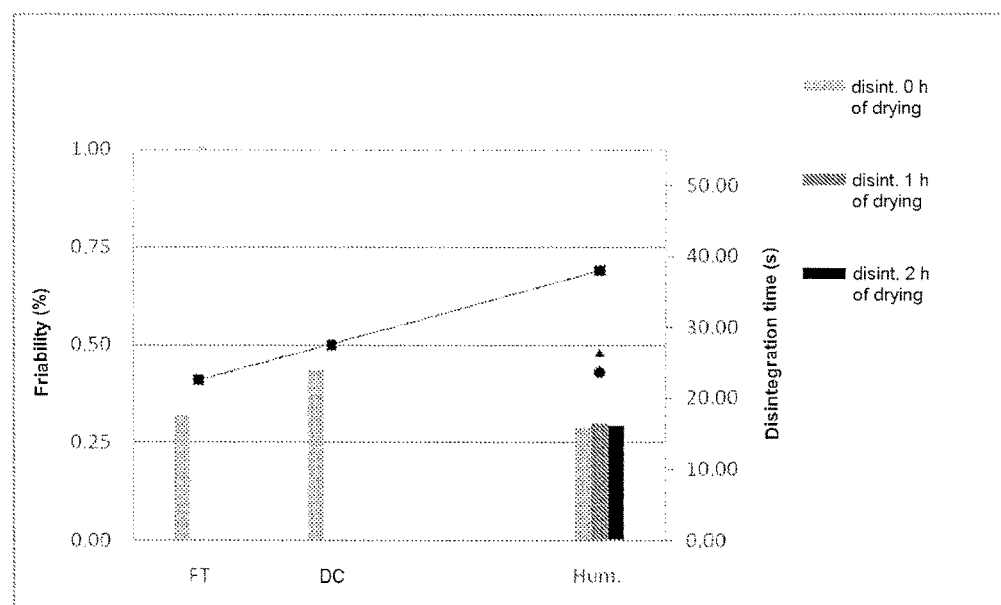
FIG. 3 represents the friability and the in vitro disintegration time of the "FT", "DC" and "Hum" orodispersible tablets having a hardness of 50 N.
Figure 4:
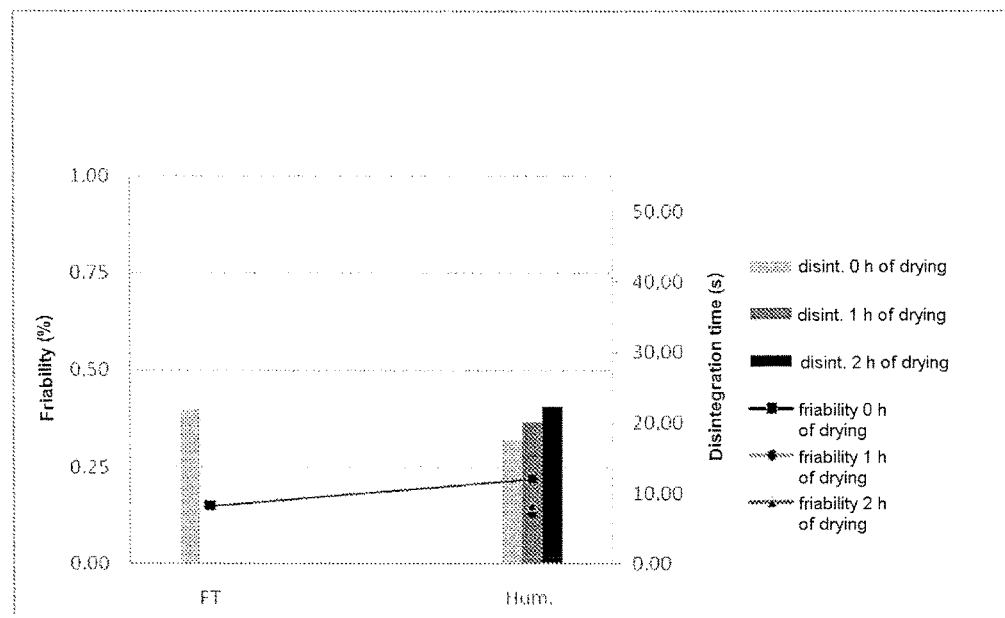
FIG. 4 represents the friability and the in vitro disintegration time of the "FT", "DC" and "Hum" orodispersible tablets having a hardness of 70 N.

The results obtained in terms of friability and of in vitro disintegration time presenting, respectively, a hardness of 50 N and 70 N are represented in FIGS. 3 (50 N) and 4 (70 N), after 0, 1 or 2 h of drying.

For the 50 N tablets (FIG. 3), the friability of the ODT DCs and of the ODT Hums without final drying (non-dried ODT Hums) is increased relative to that of the ODT FTs.

On the other hand, the friability of the ODT Hums after drying (dried ODT Hums) remains similar to that of the ODT FTs.

Similarly, for the 70 N tablets (FIG. 4), the friability of the ODT Hums after drying (dried ODT Hums) remains similar to that of the ODT FTs.

As regards the in vitro disintegration time of the tablets, it is increased by direct compression, whereas a decrease by humidification, at 50 and 70 N is noted. This decrease is smaller after drying of the tablets.

Figure 5:
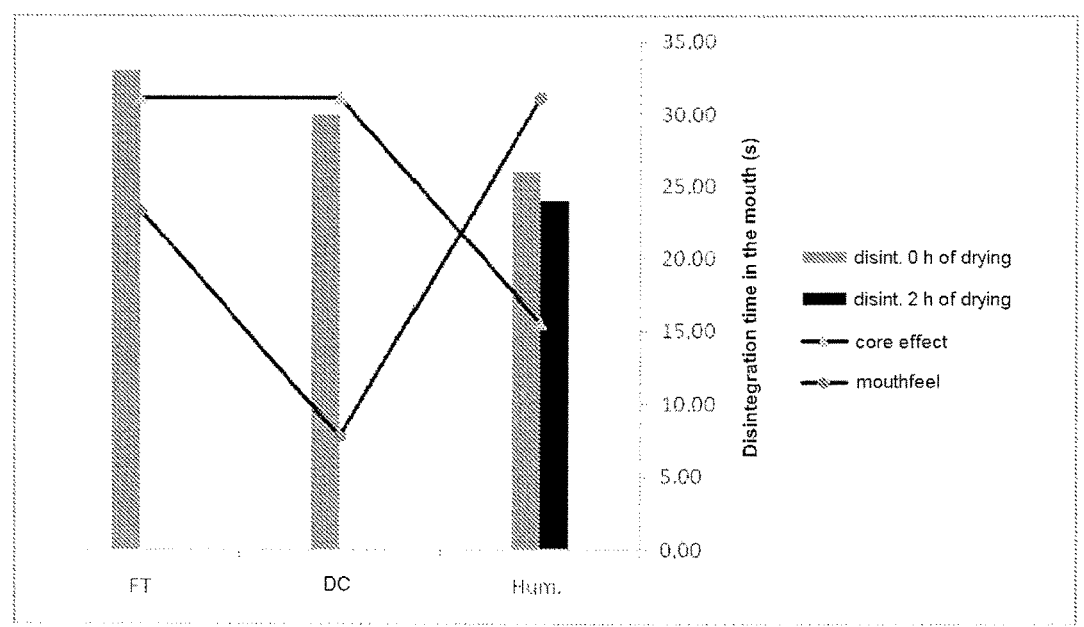
FIG. 5 represents the results of the in vivo tests (core effect, in vivo mouthfeel and disintegration time) of the "FT", "DC" and "Hum" orodispersible tablets having a hardness of 50 N.

FIG. 5 gives the results of the in vivo tests (core effect, mouthfeel and in vivo disintegration time) of the ODT FT, ODT DC and ODT Hum at 50 N. The core effect and the mouthfeel were sparingly different before and after drying of the tablets.

It emerges from these tests that the compression molding method by humidification advantageously makes it possible:
- to reduce the core effect of the tablets (which is sought to be the least possible)
- to improve the mouthfeel (which is sought to be the best possible).

Moreover, a fairly large decrease in the disintegration time in the mouth is also noted for the tablets according to the invention. The results are quite similar before and after drying.

In conclusion, the process of the invention makes it possible to reduce the in vitro and in vivo disintegration time of the tablets without having an impact on their friability. This method also makes it possible to improve the mouthfeel and to reduce the core effect, which are very important parameters for good patient compliance.

Example 3

Tablets according to the invention are prepared, using Syloid 244FP as flow agent both in the wet excipient grains and directly in the mixture for compression.

Tables 15 and 16 below represent, respectively, the percentage composition of the wet mixture of excipients, in the form of wet grains, and that of the mixture for compression.

TABLE 15

| Names | Percentages (dry extract) | Percentages |
|---|---|---|
| Mannitol 60 | 71.14 | 69.59 |
| Polyplasdone XL | 17.85 | 17.46 |
| Aspartame | 3.36 | 3.29 |
| L-HPC LH 21 | 6.31 | 6.17 |

TABLE 15-continued

| Names | Percentages (dry extract) | Percentages |
|---|---|---|
| Syloid 244FP | 1.34 | 1.31 |
| Water | | 2.22 |
| Total | 100.00 | 100 |

TABLE 16

| Names | Percentages |
|---|---|
| Neutrals 500/600 | 20.09 |
| Wet mixture of excipients (in the form of grains) | 76.00 |
| Syloid 244FP | 1.95 |
| Pruv ® | 1.95 |
| Total | 100.00 |

Table 17 below represents the residual humidity values measured for the wet mixture of excipients in the form of grains and for the mixture for compression, the compositions of which are given in tables 15 and 16, respectively.

TABLE 17

| | LOD (%) | KF (%) |
|---|---|---|
| Mixture of wet excipients | 3.0 | 2.9 |
| Mixture for compression | 2.6 | 2.7 |

Table 18 indicates the characteristics of the dried and non-dried ODT Hums, comprising Syloid 244FP as flow agent (see tables 15 and 16), as a function of the compression force exerted and of the drying time.

TABLE 18

| Hardness (N) | Compression force (kN) | Drying (h) | Mass (mg) | Thickness (mm) | Friability (%) | in vitro disint. (s) min | in vitro disint. (s) max | Flow of the mixture |
|---|---|---|---|---|---|---|---|---|
| 48 | 12.5 | 0 | 450 | 3.26 | 0.69 | 13.6 | 15.8 | to be |
| 43 | | 1 | 444 | 3.27 | 0.43 | 13.6 | 16.5 | improved |
| 41 | | 2 | 444 | 3.26 | 0.48 | 14.4 | 16.2 | |
| 73 | 16.4 | 0 | 450 | 3.16 | 0.22 | 13.7 | 17.6 | |
| 59 | | 1 | 443 | 3.16 | 0.13 | 15.8 | 20.1 | |
| 56 | | 2 | 439 | 3.42 | 0.07 | 16.0 | 17.8 | |

Example 4

Example 3 was reproduced, replacing the Syloid 244FP with Aerosil® 200.

Table 23 represents the in vivo tests of the ODT Hums thus obtained.

Tables 19 and 20 below represent, respectively, the percentage composition of the wet mixture of excipients in the form of grains and that of the mixture for compression.

TABLE 19

Formula of the excipient grains

| Names | Percentages (dry extract) | Percentages |
|---|---|---|
| Mannitol 60 | 71.14 | 69.37 |
| Polyplasdone XL | 17.85 | 17.41 |
| Aspartame | 3.36 | 3.28 |
| L-HPC LH 21 | 6.31 | 6.15 |

TABLE 19-continued

Formula of the excipient grains

| Names | Percentages (dry extract) | Percentages |
|---|---|---|
| Aerosil ® 200 | 1.34 | 1.31 |
| Water |  | 2.55 |
| Total | 100.00 | 100.00 |

TABLE 20

Formula of the mixture for compression

| Names | Percentages |
|---|---|
| Neutral 500/600 | 20.09 |
| Excipient grains | 76.00 |
| Aerosil ® 200 | 1.95 |
| Pruv ® | 1.95 |
| Total | 100.00 |

Table 21 below represents the residual humidity values measured for the wet mixture of excipients, in the form of grains, and for the mixture for compression, the compositions of which are given in tables 19 and 20, respectively.

TABLE 21

|  | LOD (%) | KF (%) |
|---|---|---|
| Wet mixture of excipients | 2.9 | 2.9 |
| Mixture for compression | 3.0 | 2.6 |

Table 22 indicates the characteristics of the dried and non-dried ODT Hums, comprising Aerosil® 200 as flow agent (see tables 19 and 20), as a function of the compression force exerted and of the drying time.

TABLE 22

| Hardness (N) | Compression force (kN) | Drying (h) | Mass (mg) | Thickness (mm) | Friability (%) | in vitro disint. (s) min | in vitro disint. (s) max | Flow of the mixture |
|---|---|---|---|---|---|---|---|---|
| 52 | 14.2 | 0 | 454 | 3.35 | 0.63 | 14.5 | 16.6 | to be |
| 36 |  | 1 | 442 | 3.37 | 0.49 | 16.9 | 18.8 | improved |
| 37 |  | 2 | 446 | 3.36 | 0.39 | 16.3 | 19.0 |  |
| 66 | 17.5 | 0 | 451 | 3.28 | 0.22 | 14.4 | 16.1 |  |
| 50 |  | 1 | 442 | 3.29 | 0.13 | 17.0 | 18.8 |  |
| 47 |  | 2 | 339 | 3.28 | 0.13 | 16.7 | 18.8 |  |

TABLE 23

ODT Hum with Aerosil ® 200

| Hardness (N) | Drying time (h) | Disint. in mouth (s) | Core effect | Mouthfeel |
|---|---|---|---|---|
| 50 | 0 | 28 | Little or none | Quite pleasant |
|  | 2 | 29 | Little or none | Slightly pasty |
| 70 | 0 | 27 | Little or none | Pleasant texture |
|  | 2 | 24 | Little or none | Pleasant texture |

Replacing the Syloid® 244 FP with Aerosil® 200 in the ODT Hums has little influence on the friability, the disintegration time and the mouthfeel for tablets at 50 N.

At 70 N, the ODT Hums containing Aerosil® 200 have a shorter disintegration time and less of a core effect than the ODT Hums containing Syloid® 244 FP.

Example 5

Tablets according to the invention are prepared using as wetting solution an aqueous solution of Gelucire® 44/14 at two different concentrations: 5% (m/m) and 15% (m/m). The Gelucire® 44/14 serves as a humectant for the mixture of excipients.

Example 5.1: Aqueous Solution Containing 5% Gelucire® 44/14

Table 20 represents the percentage composition of the wet mixture of excipients in the form of grains.

TABLE 20

| Names | Percentages of dry extract | Percentages |
|---|---|---|
| Mannitol 60 | 71.06 | 69.29 |
| Polyplasdone XL | 17.83 | 17.39 |
| Aspartame | 3.35 | 3.27 |
| L-HPC LH 21 | 6.30 | 6.14 |
| Aerosil ® 200 | 1.34 | 1.31 |
| Solution of Gelucire ® 44/14 at 5% m/m | 0.12 | 2.55 |
| Total | 100.00 | 100.00 |

Table 21 represents the composition of the mixture for compression molding.

TABLE 21

| Names | Percentages |
|---|---|
| Neutrals 500/600 | 20.09 |
| Grains of excipients | 76.00 |
| Aerosil ® 200 | 1.95 |
| Pruv ® | 1.95 |
| Total | 100.00 |

Table 22 below represents the residual humidity values measured for the mixture of excipients in the form of grains and for the mixture for compression.

TABLE 22

|  | LOD (%) | KF (%) |
|---|---|---|
| Mixture of excipients in the form of grains | 2.9 | 3.0 |
| Mixture for compression | 2.9 | 2.5 |

Table 23 below indicates the characteristics of the dried and non-dried ODT Hums, obtained with an aqueous solution of Gelucire® 44/14 at 5% as humectant, as a function of the compression force exerted and of the drying time.

TABLE 23

| Hardness (N) | Compression force (kN) | Drying (h) | Mass (mg) | Thickness (mm) | Friability (%) | in vitro disint. (s) min | in vitro disint. (s) max | Flow of the mixture |
|---|---|---|---|---|---|---|---|---|
| 51 | 14.0 | 0 | 449 | 3.34 | 0.76 | 14.8 | 16.5 | to be |
| 37 |  | 1 | 442 | 3.36 | 0.74 | 15.6 | 17.0 | improved |
| 34 |  | 2 | 441 | 3.36 | 0.77 | 14.8 | 17.6 |  |
| 69 | 18.9 | 0 | 446 | 3.24 | 0.19 | 14.7 | 18.3 |  |
| 56 |  | 1 | 444 | 3.27 | 0.13 | 15.6 | 18.0 |  |
| 53 |  | 2 | 441 | 3.27 | 0.16 | 16.3 | 19.6 |  |

Table 24 below represents the in vivo tests for the ODT Hums comprising an aqueous solution of Gelucire® 44/14 at 5% as humectant.

TABLE 24

| Hardness (N) | Drying time (h) | Disint. in mouth (s) | Core effect | Mouthfeel |
|---|---|---|---|---|
| 50 | 0 | 22 | Little or none | Pleasant texture |
|  | 2 | 22 | Little or none | Pleasant texture |

Example 5.2: Solution of Gelucire® 44/14 at 15%

Tables 25 and 26 below represent, respectively, the composition of the excipient grains and that of the mixture for compression, when an aqueous solution containing 15% Gelucire® 44/14 is used.

TABLE 25

| Names | Percentages of dry extract | Percentages |
|---|---|---|
| Mannitol 60 | 71.06 | 69.21 |
| Polyplasdone XL | 17.83 | 17.36 |
| Aspartame | 3.35 | 3.26 |
| L-HPC LH 21 | 6.30 | 6.14 |
| Aerosil ® 200 | 1.34 | 1.30 |
| Solution of Gelucire ® 44/14 at 15% m/m |  | 2.68 |
| Total | 100.00 | 100.00 |

TABLE 26

| Names | Percentages |
|---|---|
| Neutrals 500/600 | 20.09 |
| Excipient grains | 76.00 |
| Aerosil ® 200 | 1.95 |
| Pruv ® | 1.95 |
| Total | 100.00 |

Table 27 below represents the residual humidity values measured for the mixture of excipients, in the form of grains, and for the mixture for compression, the compositions of which are given in tables 25 and 26, respectively.

TABLE 27

|  | LOD (%) | KF (%) |
|---|---|---|
| Mixture of excipients in the form of grains | 2.9 | 3.1 |
| Mixture for compression | 2.5 | 2.5 |

Table 28 below indicates the characteristics of the dried and non-dried ODT Hums, obtained for a solution of Gelucire® 44/14 at 15% as humectant, as a function of the compression force exerted and of the drying time.

TABLE 28

| Hardness (N) | Compression force (kN) | Drying (h) | Mass (mg) | Thickness (mm) | Friability (%) | in vitro disint. (s) min | in vitro disint. (s) max |
|---|---|---|---|---|---|---|---|
| 50 | 14.8 | 0 | 454 | 3.37 | 0.82 | 15.0 | 17.0 |
| 36 |  | 1 | 449 | 3.37 | 0.73 | 17.2 | 18.9 |
| 34 |  | 2 | 447 | 3.35 | 0.81 | 15.7 | 18.5 |
| 74 | 20.3 | 0 | 456 | 3.29 | 0.23 | 15.6 | 17.4 |
| 54 |  | 1 | 448 | 3.31 | 0.18 | 16.8 | 18.0 |
| 52 |  | 2 | 447 | 3.28 | 0.22 | 17.5 | 18.9 |

Table 29 below represents the in vivo tests for the ODT Hums comprising a solution of Gelucire® 44/14 at 15% as humectant.

TABLE 29

| Hardness (N) | Drying time (h) | Disint. in mouth (s) | Core effect | Mouthfeel |
|---|---|---|---|---|
| 50 | 0 | 21 | Little or none | Pleasant texture |
|  | 2 | 24 | Little or none | Pleasant texture |

There is no notable difference between the ODT Hums comprising a solution of Gelucire® 44/14 at 5% or at 15%, in terms of friability and disintegration time.

The disintegration times of the ODT Hums are similar to those of the ODT FTs for the ODT Hums at 50 N, and slightly shorter for the ODT Hums at 70 N.

As regards the in vivo tests, the use of Gelucire® 44/14 makes it possible to reduce the core effect in the mouth. The actual texture of the tablet is appreciated.

What is claimed is:

1. A compression molding process for preparing an orodispersible tablet, comprising the steps of:
    preparing using a humidification method a wet mixture of excipients consisting of from 65 wt % to 90 wt % diluent based on a total weight of the wet mixture of excipients, a disintegrant, a sweetener, a binder, and less than 3 wt % of a humectant based on a total weight of the wet mixture of excipients, said excipients being in the form of grains, wherein the humectant is macrogol glyceride, and wherein the wet mixture of excipients has a residual humidity or water content of from 2% to 3%;
    preparing coated microcrystals or microgranules of active principle;
    mixing the coated microcrystals or microgranules of active principle with the wet mixture of excipients to obtain a mixture for compression; and
    compressing the mixture for compression to obtain a tablet.

2. A process according to claim 1, the process further comprising the steps of:
    adding to the mixture for compression at least one excipient chosen from the group consisting of a flow agent, a lubricant, a flavoring agent, a sweetener, a colorant and mixtures thereof; and
    drying the tablet after compression.

3. A compression molding process for preparing an orodispersible tablet, comprising the steps of:
    preparing a mixture of excipients consisting of from 65 wt % to 90 wt % diluent based on a total weight of the mixture of excipients, a disintegrant, a sweetener, a binder, optionally a flow agent, optionally a lubricant, optionally a flavoring agent, and optionally a colorant, said excipients being in form of grains;
    incorporating a wetting solution into said mixture of excipients in an amount sufficient to obtain a wet mixture of excipients having a residual humidity or water content of from 0.5% to 7%, said wetting solution comprising a humectant chosen from the group consisting of poloxamers, macrogols, macrogol glycerides, and polysorbates;
    preparing coated microcrystals or microgranules of active principle;
    mixing the coated microcrystals or microgranules of active principle with the wet mixture of excipients to obtain a mixture for compression; and
    compressing the mixture for compression to obtain a tablet.

* * * * *